United States Patent
Al-Abdulla et al.

(10) Patent No.: US 8,133,210 B2
(45) Date of Patent: Mar. 13, 2012

(54) AQUEOUS OPHTHALMIC SPRAY AND METHOD FOR DELIVERY OF ARTIFICIAL TEARS TO THE OCULAR SURFACE

(76) Inventors: Nael A. Al-Abdulla, Towson, MD (US); Lee A. Snyder, Baltimore, MD (US)

( * ) Notice: Subject to any disclaimer, the term of this patent is extended or adjusted under 35 U.S.C. 154(b) by 0 days.

(21) Appl. No.: 10/693,179

(22) Filed: Oct. 23, 2003

(65) Prior Publication Data

US 2004/0138630 A1    Jul. 15, 2004

Related U.S. Application Data

(60) Provisional application No. 60/420,556, filed on Oct. 23, 2002.

(51) Int. Cl.
*A61M 35/00* (2006.01)

(52) U.S. Cl. .......................... 604/294; 604/295; 604/300

(58) Field of Classification Search .......... 604/294–296, 604/300–302; 222/383.1, 523, 525–527, 222/420
See application file for complete search history.

(56) References Cited

U.S. PATENT DOCUMENTS

| | | | | |
|---|---|---|---|---|
| 4,175,704 A * | 11/1979 | Cohen | ............ | 239/320 |
| 4,946,452 A * | 8/1990 | Py | ................ | 604/301 |
| 5,059,188 A * | 10/1991 | Goddard | ....... | 604/300 |
| 5,201,726 A * | 4/1993 | Kirkham | ....... | 604/294 |
| 5,588,564 A * | 12/1996 | Hutson et al. | ....... | 222/383.1 |
| 6,041,978 A | 3/2000 | Hagele | | |
| 6,336,917 B1 | 1/2002 | Berke | | |

* cited by examiner

Primary Examiner — Michele M Kidwell
(74) Attorney, Agent, or Firm — Edwards Wildman Palmer LLP; Peter F. Corless; Lisa Swiszcz

(57) ABSTRACT

A delivery device and method for the delivery of a substance to the eye or other bodily site of a user. The device delivers the substance to the eye in the form of a non-aerosol spray or mist. The delivery device is particularly suitable for the delivery of artificial tear compositions to the ocular surface.

54 Claims, 3 Drawing Sheets

AQUEOUS OPHTHALMIC SPRAY AND METHOD FOR DELIVERY OF ARTIFICIAL TEARS TO THE OCULAR SURFACE

The present application claims the benefit of U.S. provisional application No. 60/420,556, filed on Oct. 23, 2002, the teachings of which are incorporated herein by reference.

FIELD OF THE INVENTION

The present invention relates to improved devices and methods for the delivery of a substance to the eye. More particularly, the present invention relates to a device and method that delivers artificial tear compositions, also known as ocular demulcent compositions, to the ocular surface, wherein the compositions are delivered in the form of a spray or mist.

BACKGROUND OF THE INVENTION

Dry eyes is a widespread condition with a prevalence of approximately 14% in a recent population-based cohort (Moss S E, Klein R, and Klein B E, Archives of Ophthalmololgy 118:1264-8, 2000). Dry eyes affects people of all ages, and is most frequently observed in older patients.

Mechanisms for dry eyes include: 1) increased tear evaporation, which for example occurs in low-humidity environments or results from eye lid abnormalities with exposure of; 2) decreased tear production, which for example occurs during the use of systemic medications or results from lacrimal gland diseases; or, 3) unstable tear film, which for example occurs during contact lens wear or results from blepharitis, a common eyelid disorder. Symptoms include redness, foreign body or gritty sensation in the eye, burning sensation, and blurring of vision. The irritation may be mild or disabling. The loss of vision may be devastating.

Treatment is focused on replacing the tears, preventing their loss, and protecting the ocular surface. Artificial tears is among the most common treatment modalities aimed at replacing the aqueous tears onto the ocular surface. Artificial tears, also known as demulcents, is defined by the U.S. Food and Drug Administration as, "An agent, usually a water-soluble polymer, which is applied topically to the eye to protect and lubricate mucous membrane surfaces and relieve dryness and irritation" (Code of Federal Regulation, Title 21, Part 349, Subpart A, Section 349.3 a). Artificial tears is an aqueous balanced salt solution with an agent such as hydroxymethyl cellulose, hydroxypropyl cellulose, hydroxypropyl methylcellulose, methylcellulose, and or polyvinyl alcohol.

Currently, artificial tears for public consumption are available only in a topical drop form for delivery. However, proper administration of topical drops requires an individual to recline one's head back such that the ocular surface is looking upwards towards the sky. If the head is not reclined adequately, the drop will roll off the eyelid or even completely miss the ocular surface. As a result, repeated application of drops is required until proper positioning of the ocular surface is obtained and sufficient amounts of the drops are delivered. This not only results in a waste of the artificial tears, but also is inconvenient for a user to continue to apply drops and recline his or her head until sufficient drops are delivered. Further, such a method for delivery can be difficult, particularly for the elderly, the disabled and for young children.

Liquid compositions have generally been delivered to various bodily sites in various forms including, for example, aerosol sprays and sprays delivered using electrical forces. However, the use of such sprays provides a number of drawbacks.

An aerosol or aerosol product, as referenced herein, is defined by the Code of Federal Regulations as follows, "Aerosol shall mean a material which is dispensed from its container as a mist, spray, or foam by a propellant under pressure" (Code of Federal Regulation, Title 29, Chapter 17, Part 1910, Section 1910.106). A further specification of the definition is as follows: "Aerosol product means a product characterized by a pressurized spray system that dispenses product ingredients in aerosol form by means of a propellant (i.e., a liquefied or compressed gas that is used in whole or in part, such as a co-solvent, to expel a liquid or any other material from the same self-pressurized container or from a separate container) or mechanically induced force. 'Aerosol product' does not include pump sprays." (Code of Federal Regulation, Title 40, Chapter 1, Part 59, Section 59.202). In referencing the propellant, "Aerosol means any non-refillable receptacle containing a gas compressed, liquefied or dissolved under pressure, the sole purpose of which is to expel a nonpoisonous (other than a Division 6.1 Packing Group III material) liquid, paste, or powder and fitted with a self-closing release device allowing the contents to be ejected by the gas" (Code of Federal Regulation, Title 49, Chapter 1, Part 171, Section 171.8). As referenced herein, an aerosol is defined in any or all of the above terms.

Thus, an aerosol spray requires a propellant as an additional ingredient. When delivering a substance to the body for a particular purpose, it would be desirable to eliminate the use of any ingredients unnecessary for that particular purpose. Additional, unnecessary ingredients can ultimately have an adverse affect on the body. Thus, the additional ingredients must undergo rigorous tests to ensure that they will not adversely affect the body. Such tests require a substantial amount of time and money. Further, tests are not always 100% accurate and cannot possibly take into account every possible variable that may impact each and every individual. Still further, the use of additional, unnecessary ingredients adds to the cost of the compositions since additional ingredients must be obtained. In addition, the stability of the compositions can be adversely affected due to the combination of multiple ingredients. Further, additional ingredients may not always be successfully mixed with the compositions (e.g. artificial tear compositions) and, thus, tests must be performed to ensure that these ingredients will mix with and form a uniform mixture with the compositions to prevent delivery of substances having inconsistent ingredients. For example, if the composition (e.g. artificial tear composition) does not mix adequately with the additional ingredients (e.g. propellant formulation), the composition delivered may be primarily a propellant formulation at some times and primarily an artificial tear composition at other times. In fact, the U.S. Food and Drug Administration has removed certain aerosol products from the market, due to the unsafe nature of the aerosol propellant. These aerosol products with propellants include, but are not limited to, trichloroethane, vinyl chloride, and zirconium (Code of Federal Regulation, Title 21, Chapter 1, Part 216, Section 216.24). Currently, aerosol products are not permitted for ophthalmic/ocular use due to their unsafe nature because of the presence of propellant. Further, the use of aerosols may be discouraged, in general, due to potential unfavorable impact on the environment by the propellant. For these reasons and due to the delicate nature of the eye area, aerosol spray delivery of substances is not permitted for ophthalmic/ocular use.

Aerosol sprays and sprays that are delivered using, for example, piezoelectric or electromagnetic transducers are also unsafe for ophthalmic/ocular use. Such sprays deliver substances with excessive force, which would cause discomfort to the eye and could damage the delicate eye area resulting in keratopathy. As noted by MacLean, the extent of aerosol keratopathy is proportional to the force of impact of the agent onto the corneal surface (MacLean A L, American Journal of Ophthalmology 63:170919, 1967; MacLean A L, Transactions of the American Academy of Ophthalmology and Otolaryngology, 71:330-40, 1967). The keratopathy is often a mild and transient phenomenon, but can be severe, especially in patients with dry eyes whose ocular surface is abnormal and prone to easy injury.

SUMMARY OF THE INVENTION

The present invention provides a novel device and method for the delivery of substances which reduces or overcomes many deficiencies of prior art devices. More particularly, the present invention relates to a device and method that delivers an aqueous ophthalmic composition, specifically artificial tears or demulcent solutions, to the ocular surface. The device and methods deliver the compositions in the form of a spray or mist, preferably using a non-aerosol, non-electrically produced force.

In summary, there are several advantages of the present invention of spray delivery of artificial tears:

(1) With the topical eye drops that are currently available for use, the drop must be held in close proximity to the eye in order to dispense it properly onto the ocular surface. There are numerous reports of "microbial contamination of in-use ocular medications" (Schein O D, et al., Archives of Ophthalmology 110:82-5, 1992) and "bacterial contamination of drops and dropper tips of in-use multidose eye drop bottles" (Hovding G and Sjursen H, Acta Ophthalmologica 60:213-22, 1982). The present device provides a simple non-contact topical method of delivery of artificial tears to the ocular surface in a generally horizontal direction. Further, the present invention does not require close positioning to the eye for proper administration. By holding the device of the present invention in front of the eye with the head positioned in a generally forward/horizontal direction (i.e., with the eyes looking forward rather than upward) and by holding the device further away from the ocular surface, the risk that the device will touch the ocular surface is reduced, and, thus, there is a reduction in risk of ocular surface infections.

(2) Proper administration of topical eye drops using currently available techniques requires an individual to recline one's head back such that the ocular surface is looking upward towards the sky. If the head is not reclined adequately, the drop will roll off the eyelid or even completely miss the ocular surface. As a result, repeated application of drops is required until proper positioning of the ocular surface is obtained and sufficient amounts of the drops are delivered. This results in a waste of the artificial tears. By providing a device that delivers the ocular composition to the eye in a generally horizontal position, the artificial tears solution is more successfully applied to the ocular surface.

(3) Administration of topical eye drops using currently available devices is inconvenient because a user must recline his or her head until sufficient drops are delivered. Such a topical eye drop method for delivery is difficult, particularly for the elderly or the disabled who are unable to recline their heads back and for young children who may not wish to recline their heads back. The present invention solves this problem by allowing the artificial tears solution to be delivered to the ocular surface from a horizontal position of the application. By providing a device that can be applied to the eye when the head is in a generally forward/horizontal direction (i.e., with the eyes looking forward rather than upward), delivery of artificial tears solution is easier and more convenient for all users.

(4) The present invention provides for a non-aerosol and non-electrically produced (e.g., non-piezoelectric and non-electromagnetic) form of spray or mist, which decreases the risk of keratopathy from the force of aerosol or electrically produced sprays or mists.

(5) The present invention provides for a non-aerosol form of spray or mist of artificial tears, which decreases the risk associated with the addition of a propellant.

One embodiment of the present invention provides a simple and novel system for the delivery of artificial tears. The artificial tears spray delivery system allows all patients, whether elderly and disabled or young and healthy, to obtain with ease and soothing comfort a delivery of artificial tears to their ocular surfaces, treating a potentially debilitating condition.

Preferably, the device comprises a hand-held housing having a non-aerosol mechanism for the delivery of the composition. The housing preferably delivers the composition without the aid of piezoelectric or electromagnetic transducers. The mechanism for delivery in accordance with the present invention is specifically designed by the fact that it does not utilize an aerosol or electrically (e.g., piezoelectric or electromagnetic) produced force. This minimizes the force of impact of the delivered spray or mist, thereby minimizing discomfort to the eye and preventing keratopathy. In particular, the device of the present invention is capable of delivering the composition to the eye in the form of a spray or mist having a force less than that of an aerosol or electrically produced spray or mist.

In one embodiment, the device of the present invention is adapted for the delivery of a substance to the eye and generally comprises: a housing for holding the substance, at least one outlet port through which the substance is delivered from the device to the eye, and a non-aerosol, non-electric delivery mechanism. The device delivers the substance to the eye in the form of a spray or mist. Preferably, the device delivers an artificial tear or demulcent composition to the eye. During use, the head is positioned facing forward and the device positioned in front of the eye so that the spray of mist is delivered to the eye in a substantially horizontal direction. Thus, in this embodiment, the force of the spray or mist delivered by the device is sufficient to deliver the spray or mist to the eye without the aid of gravity.

The housing can be hollow and the substance contained within the hollow of the housing or, for example, the housing may contain a reservoir that holds the substance. The housing is preferably fabricated so as to prevent collapse during use. Thus, for example, the housing can be fabricated of a rigid material that prevents collapse and/or the walls forming the housing can be fabricated to have a thickness sufficient to prevent collapse of the housing during use. In a preferred embodiment, the housing is fabricated of a translucent material and is cylindrical in shape.

In an exemplary embodiment, the non-aerosol, non-electric delivery mechanism comprises the outlet port in connection with a spray nozzle. The delivery mechanism can further include a pump or similar mechanism, which assists in moving the composition from within the housing and out of the device. The pump is preferably a non-aerosol mechanism, which assists in minimizing the force of impact of the delivered spray or mist. The pump is also preferably a non-electrically produced pump (e.g. non-piezoelectric or non-electromagnetic). The delivery mechanism can further include a tubular portion or similar conveyance mechanism that extends from the outlet and/or spray nozzle into the housing such that actuation of the device (e.g. pump) causes the substance to be drawn in through the tubular portion, through the spray nozzle and out of the outlet. The tubular portion can be, for example, a straw-like tube having a circular or any other geometrically shaped cross-section.

In one embodiment, the delivery mechanism includes an actuation mechanism, in connection with the delivery mechanism wherein manipulation of the actuation mechanism delivers the substance to the eye. For example, the actuation mechanism can be rotatable with respect to the housing such that rotating the actuation mechanism with respect to the housing delivers the substance to the eye. In another embodiment, the actuation mechanism is movable horizontally and/or vertically with respect to the housing such that movement of the actuation mechanism vertically or horizontally with respect to the housing delivers the substance to the eye. In one embodiment, a portion located on the top of the housing is movable with respect to the housing and, when the actuation mechanism is manipulated to actuate the device, e.g. the portion pressed downwards towards the housing or pulled upwards away form the housing, the delivery mechanism (e.g. pump) is actuated to deliver the composition. Manipulation of the actuation mechanism results in a pressure being placed on the composition in the housing. In some embodiments, the force of the spray or mist delivered can be altered by the user's manner in manipulating the actuation mechanism. For example, if the user manipulates the actuation mechanism more forcibly and/or more quickly, the force of the spray can be increased. Thus, if the actuation mechanism is a portion at the top of the housing that is movable downwards towards the housing, by pressing the portion downwards more quickly, the composition can be forced more quickly through the outlet port with more force. Conversely, by slowly depressing the portion, the composition can be forced through the outlet port more slowly and with lesser force. Further, the distance that the portion is depressed can provide varying amounts of delivered substances. While the actuation mechanism has been described as being located at the top of the housing, it is to be understood that it can be located anywhere in the device. Further, while the actuation mechanism has been described as being movable vertically with respect to the housing, it is to be understood that it can be movable and manipulated in various ways, such as, for example, rotation and horizontal movement with respect to the housing.

Until the actuation mechanism is manipulated, the composition within the container is not under pressure, and no dispensing will take place. It will also be apparent that the force of the spray or mist can be varied by the pressure applied by hand through the actuation mechanism, and that such pressure can be applied for a continuous spray or mist or intermittent spray or mist, all of which is entirely within the control of the user.

The present invention further provides for methods for delivering substances to the body, preferably to the ocular surface, wherein the substance is delivered to the ocular surface in the form of a non-aerosol, non-electrically produced spray or mist. Delivery of the substance is preferably not dependent on gravitational forces. Further, delivery of the substance to the ocular surface in preferably in the form of a spray or mist in a generally horizontal direction. The methods further comprise manipulating the force of the delivered spray or mist as required. The force can be manipulated in a number of ways such as by varying the size of the outlet port through which the substance is delivered, by varying the flow of substance through the outlet port, by varying the proximity of the outlet port with respect to the ocular surface and by varying amounts of force on the actuation mechanism.

DETAILED DESCRIPTION

Figure 1:
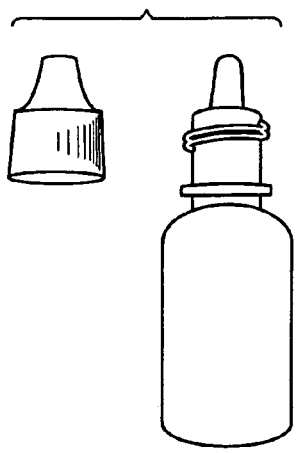
FIG. 1 shows a device currently used for the delivery of artificial tears in the form of drops.
Figure 2:
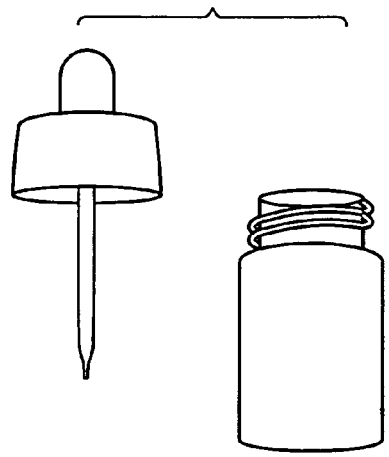
FIG. 2 shows another embodiment of a device currently used for the delivery of artificial tears in the form of drops.
Figure 3:
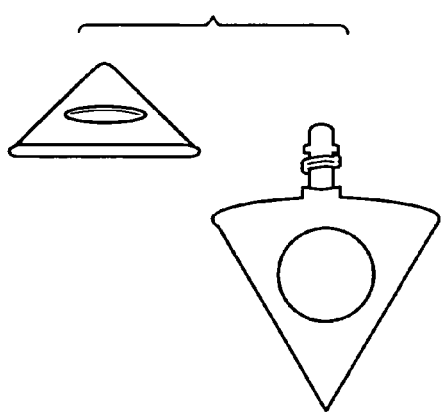
FIG. 3 shows another embodiment of a device currently used for the delivery of artificial tears in the form of drops.

Although the delivery devices and methods of the present invention are primarily illustrated and described herein by means of devices which have been adapted for delivery of an artificial tear composition to the ocular surface, it will be appreciated by those skilled in the art that such devices may also be adapted for delivery to other bodily sites and for delivery of other substances.

Referring now to the various figures of the drawing, wherein like reference characters refer to like parts, there is shown in FIGS. 4-11 various views of a delivery device 1, in accordance with the invention.

As shown in FIGS. 4-9, the delivery device 1 includes a housing 2, which is designed to contain the artificial tear composition. The overall housing can be hollow and the artificial tear composition can be contained within the hollow of the housing or, for example, the housing can contain a reservoir or portion within the housing that holds the artificial tear composition. The device 1 can be disposable or reusable. In one embodiment, the device 1 is disposable and the artificial tear composition is contained in the housing 2. When the composition has been used and the housing empty or substantially empty, the entire device can be disposed of. In one embodiment, the housing cannot be opened and refilled with solution. For example, in one embodiment, the actuator mechanism or other cap or covering for the housing or reservoir cannot be removed to allow the housing to be refilled with solution. In another embodiment, the entire device 1 or a portion of the device is reusable. For example, in one embodiment, the housing 2 holds the composition and is refillable. Thus, the housing 2 includes an opening or it can be opened and sealed when required so that additional composition can be added when required. In one embodiment, for example, the actuation mechanism, e.g. spray nozzle, is removable so that the composition can be added through this portion of the device. In another embodiment, cartridges or similar containers holding the composition fit within the housing. When required, used cartridges are removed and new cartridges are placed in the housing 2. In yet another embodiment, the housing can be removable and replaceable with new housings holding the substance.

The housing 2 can be formed of any materials that retain the sterility of the contents and, preferably, is formed of a relatively rigid material and/or of a material having a thickness sufficient to provide the device with rigidity sufficient to prevent collapse of the housing during use. For example, the housing can be fabricated of glass, plastics, metals, and other materials conventionally used to house artificial tears and other substances delivered to the eyes and other body parts. Further, the housing can be opaque or it can be translucent to enable a user to view the amount of artificial tear composition remaining. In some embodiments, the housing can include markings that indicate to a user the volume and/or approximately how many sprays or "doses" remain. In one preferred embodiment, the housing is fabricated of a translucent plastic.

Figure 4:
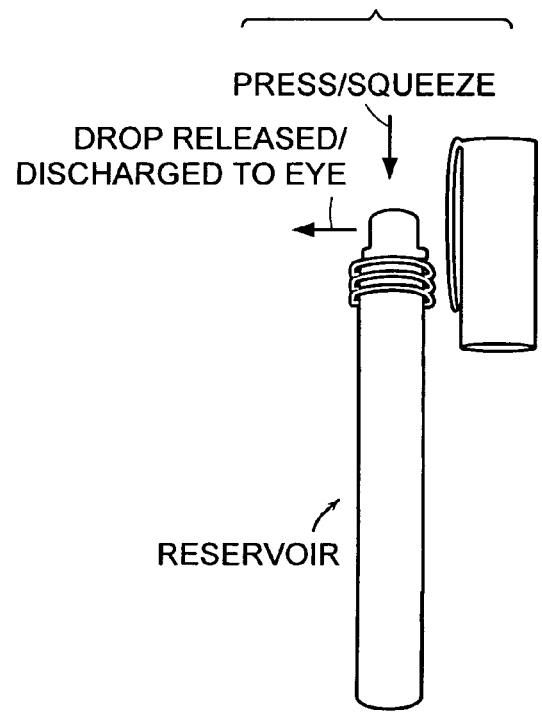
FIG. 4 shows one embodiment of the present delivery device.

The delivery device 1 and housing 2 can be of any shape and size. Preferably, the delivery device 1 is a portable, handheld, hand-operated device and, thus, the device 1 and housing 2 are preferably sized and shaped to conveniently fit within a user's hand. For example, in one preferred embodiment as shown in FIG. 4, the housing 2 and overall device 1 is cylindrical in shape. However, any other shapes could be employed such as, for example, rectangular in shape, elongate and octagonal in cross-section, elongate and triangular in cross section, bullet-like in shape, etc. The size of the housing 2 can vary and preferably is at least about 0.75 inches in length and at least about 0.15 inches in its greatest cross-sectional width. In a preferred embodiment, the housing is between about 0.75 inches to about 8 inches long, more preferably between about 2.5 inches to about 5 inches long. Preferably, the housing is between about 0.2 inches to about 2 inches in its greatest cross-sectional width, more preferably between about 0.25 inches to about 1 inch in its greatest cross-sectional width. The thickness of the housing walls can vary depending on the type of material used to form the housing and the thickness required to provide sufficient rigidity. In general, the thickness of the housing walls is at least about 0.1 mm. Preferably the thickness of the housing walls is between about 0.1 mm to about 3 mm, more preferably, between about between about 0.5 mm to about 1.5 mm. In general, the device is preferably designed so as to hold approximately 1 fluid ounce (30 mL) of the composition, which is the conventional amount provided with presently available devices. However, substantially more or substantially less volume can be provided and the size of the device and housing can be designed accordingly. While examples of dimensions have been described, it is to be understood that the devices of the present invention can vary in size and, thus, any dimensions in addition to those specified could be used.

The device 1 further includes a delivery mechanism 3 for delivery of the artificial tear composition from within the housing 2 and out of the device 1. The composition is preferably delivered out of the device in a spray-like or mist-like form and, thus, the delivery mechanism 3 is designed accordingly. The delivery mechanism 3 is preferably a non-aerosol delivery mechanism. The delivery mechanism 3 also preferably delivers the composition without the aid of electrically produced force (e.g., piezoelectric or electromagnetic). As such, the delivery mechanism 3 minimizes the force of impact of the delivered spray or mist, which minimizes discomfort to the eye and prevents keratopathy.

In one embodiment, the delivery mechanism 3 comprises a spray nozzle 5 having at least one outlet port 6 through which the artificial tear composition is delivered out of the device. The delivery mechanism 3 preferably also includes an actuation mechanism 4 that, when manipulated, causes the composition to be delivered out of the device 1 in a spray-like or mist-like form. For example, in one preferred embodiment, the actuation mechanism 4 comprises the spray nozzle 4. Thus, manipulation of the spray nozzle 5 causes the composition to be delivered out of the device 1. In another embodiment, the actuation mechanism is a portion 7 (e.g. extended tab, button or similar portion) on the housing 2 or connected to the housing 2, for example, the portion 7 can be positioned on the top of the housing 2. The portion 7 can be movable, for example, vertically movable, horizontally movable, rotatable, etc. with respect to the housing 2. When actuated, e.g. when the portion 7 is pressed downwards towards the housing 2, pulled upwards away form the housing 2, rotated, moved to the left or to the right with respect to the housing 2, the delivery mechanism 3 is actuated to deliver the composition out of the device 1. In a preferred embodiment, manipulation of the actuation mechanism 4 places a pressure on the composition in the housing 2. When the actuation mechanism 4 is not manipulated, the composition within the housing 2 is not under pressure, and the composition will not be delivered out of the device.

In some embodiments, the force of the spray or mist delivered from the device 1 can be increased or decreased by the user's manner in manipulating the actuation mechanism 4. For example, in one embodiment, if the user manipulates the actuation mechanism 4 more forcibly and/or more quickly, the force of the spray or mist is increased. Conversely, manipulating the actuation mechanism 4 more slowly and/or with less force, the composition can be delivered from the device more slowly and with lesser force. Further, the distance that the actuation mechanism is manipulated, e.g. the distance that the portion is depressed, can provide varying amounts of delivered substances. In some embodiments, manipulation of the actuation mechanism 4 can be performed so as to provide a continuous spray or mist or intermittent spray or mist.

Figure 5:
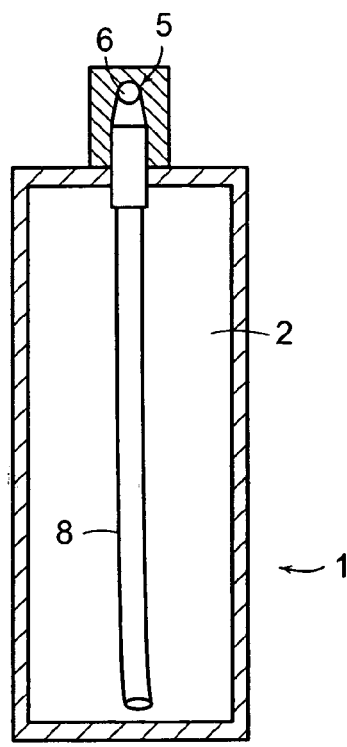
FIG. 5 is a side view of one embodiment of the delivery device in accordance with the present invention in a non-actuated state.
Figure 6:
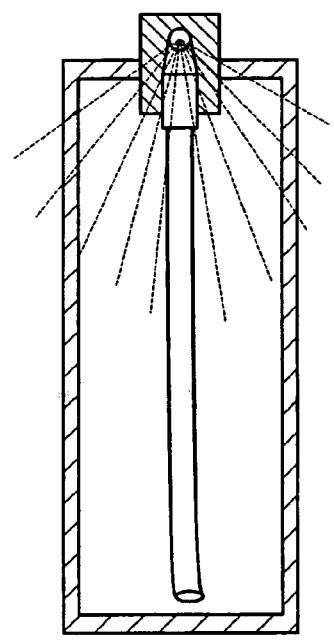
FIG. 6 is a side view of one embodiment of the delivery device in accordance with the present invention in an actuated state.
Figure 7:
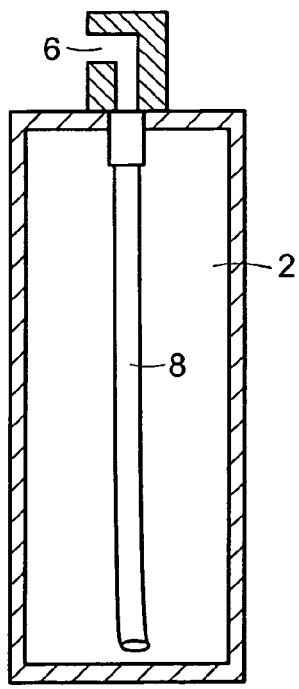
FIG. 7 is a side cross-sectional view of one embodiment of the delivery device in accordance with the present invention in a non-actuated state.
Figure 8:
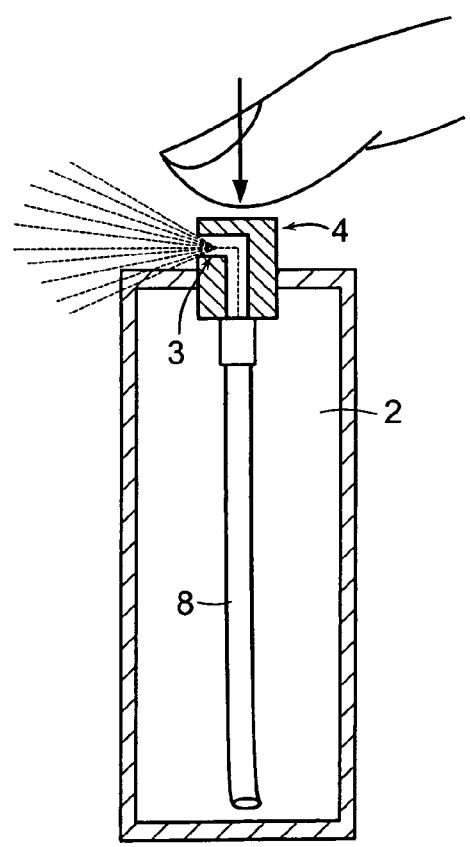
FIG. 8 is a side cross-sectional view of one embodiment of the delivery device in accordance with the present invention in an actuated state.
Figure 9:
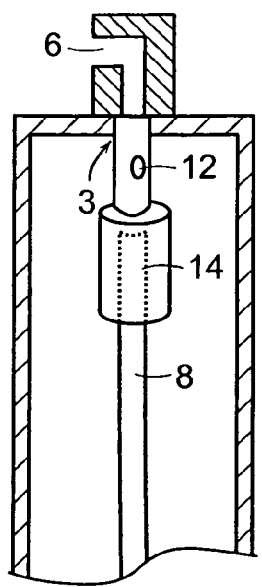
FIG. 9 shows one embodiment of the device in accordance with the present invention in a non-actuated state wherein the flowpath of the composition is incomplete/blocked.
Figure 10:
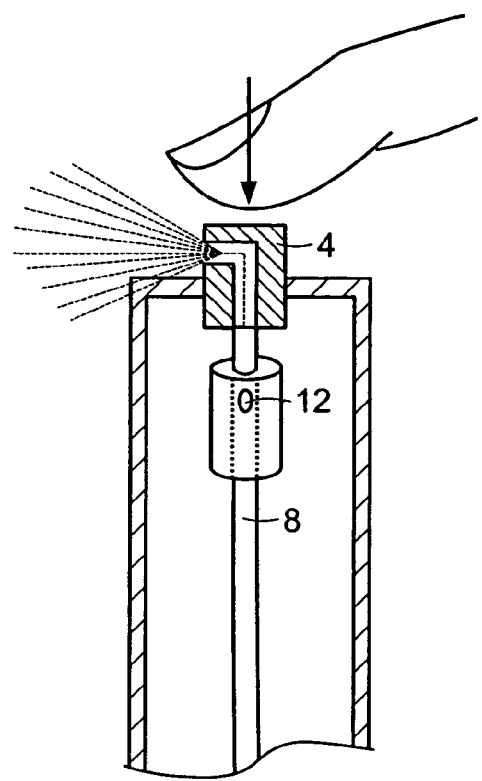
FIG. 10 shows one embodiment of the device in accordance with the present invention in a non-actuated state wherein the flowpath of the composition is complete/open.
Figure 11:
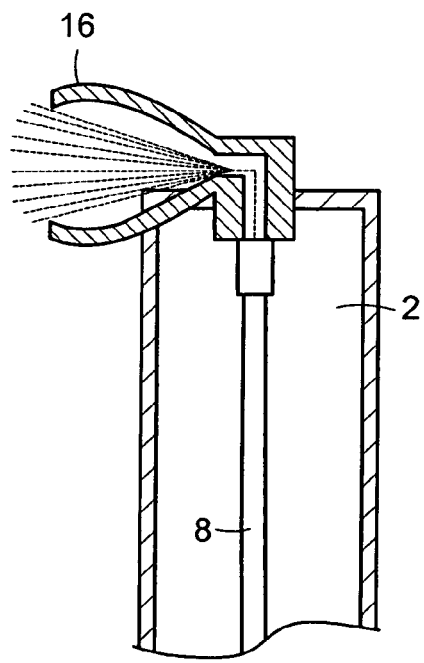
FIG. 11 shows one embodiment of the device in accordance with the present invention wherein an extension or funnel-like portion extends around the outlet of the device to assist in delivery of the substance to the proper location.

In an exemplary embodiment, the actuation mechanism 4 includes a spray nozzle 5 positioned at the top of the housing 2, as shown in FIGS. 4-10. In the embodiment shown, the actuation mechanism 4 is movable downwards towards the housing 2. The spray nozzle 5 in its non-actuated state is shown in FIGS. 5, 7 and 9. By depressing the spray nozzle 5 downwards towards the housing 2, the device is actuated to deliver artificial tears, as shown in FIGS. 6, 8 and 10.

Spray nozzles are well-known and the spray nozzles of the present invention can be in accordance with conventional spray nozzles. The present devices preferably deliver the artificial tears in the form of a spray or mist by use of non-aerosol means and, thus, the spray nozzle is in accordance with conventional non-aerosol spray nozzles.

In one embodiment, the outlet port 6 communicates with the interior of the hollow housing 2 or reservoir within the hollow housing via a tubular member 8 that extends into the housing 2. Thus, manipulation of the actuation means 4 causes artificial tears within the housing 2 to be drawn in through the tubular member 8 and out of the device through the at least one outlet port 6. The tubular member 8 can be, for example, a straw-like tube having a circular or any other geometrically shaped cross-section.

In some embodiments, the delivery mechanism 3 further includes a pump (not shown) or similar mechanism, which assists in moving the composition from within the housing 2 and out of the device 1. The pump is preferably a non-aerosol pump and operates without electrical forces (piezoelectric or electromagnetic), which assists in minimizing the force of impact of the delivered spray of mist. Pumps are used in various types of spray delivery devices and, thus, the general features of the pump may be in accordance with conventional pumps.

The device in accordance with the present invention is specifically designed to minimize the force of impact of the delivered spray or mist, thereby minimizing discomfort to the eye and preventing keratopathy. Specifically, delivery of the artificial tears is in the form of a non-aerosol non-electrically produced (e.g., non-piezoelectric and non-electromagnetic) spray or mist having a force that is adequate to deliver the artificial tears to the eye but that is inadequate to damage or cause discomfort to the delicate eye area and that prevents keratopathy. The device is preferably used by placing the outlet port in front of the eye and delivering the spray or mist in a generally horizontal direction from the device to the eye. Thus, the force of the spray or mist is such that spray or mist overcomes gravity in a manner sufficient to deliver the spray or mist to the eye.

In accordance with the present devices and methods, the spray or mist is delivered from the device 1 with force sufficient to deliver the spray or mist from the outlet port(s) 6 to the eye. This force can vary depending on the distance that the outlet port(s) 6 is in relation to the ocular surface. In typical use, the outlet port 6 is positioned approximately 5 to 30 cm away from the ocular surface and, thus, the force required for the spray or mist to reach the ocular surface would be sufficient for the spray or mist to travel this distance. The force of the spray or mist delivered can be set by manipulating the design of the device in a number of ways. For example, the force of the spray or mist can be increased and decreased by reducing and increasing, respectively, the size of the outlet port 6, while the amount of composition delivered from the device 1 through the outlet port 6 is maintained. The force of the spray or mist can also be increased and decreased by maintaining the size of the outlet port 6, while increasing and decreasing, respectively, the amount of composition delivered from the device 1 through the outlet port 6. Further, when a tubular member 8 or similar conveyance mechanism is included in the device, the diameter/cross-sectional size of the tubular member 8 or similar conveyance mechanism can be altered to modify the force of the delivered spray or mist. For example, by decreasing the cross-sectional size of the tubular member 8 through which a given amount of artificial tear composition must pass, the force is increased. Likewise, by increasing the cross-sectional size of the tubular member 8 through which a given amount of artificial tear composition must pass, the force is decreased. Further, when included, one or more pumps can be designed so as to increase or decrease the force of the spray or mist delivered. Further, if, for example, the device 1 is designed so as to deliver the artificial spray composition up to 20 cm, by positioning the device closer to the eye within this range, greater force can be delivered to the eye by the spray or mist and, by positioning the device further away from the eye within this range, lesser force can be delivered to the eye by the spray or mist.

In another embodiment, delivery mechanism 3/actuation mechanism 4 further includes a valve (not shown) that is triggered by manipulating the actuation mechanism 4, such that upon manipulation of the actuation mechanism, the valve opens and the artificial tears are delivered from the device 1. For example, the spray nozzle 5 may be in communication with the valve such that upon actuation of the actuation mechanism 4, the valve opens and artificial tears travel through and out of the device 1. The valve can, in some embodiments, be a conventional pressure-responsive valve that opens when the liquid within the housing is directed and pushed towards the valve, thereby opening the valve. This valve can be positioned anywhere in the flowpath of the composition through and out of the device 1. Thus, for example, the valve can be at the inlet of the tubular member 8 such that when the valve is closed, no composition enters the tubular member 8 and when the valve is opened, composition enters the tubular member 8 and is delivered out of the device. The valve could also be positioned anywhere along the tubular member 8. In one embodiment, a valve is located between the tubular member 8 and its connection to the spray nozzle 5 such that, when the valve opens, composition in the tubular member 8 is allowed to pass into and through the spray nozzle 5 out of the device. Still further, the valve could be positioned at the outlet port 6 such that opening of the valve allows the composition to pass out of the outlet port 6. Further a plurality of valves can be located anywhere in the device in various locations so as to permit and prevent delivery of the artificial tear composition. Valves are used in various types of delivery devices and, thus, the general features of the valves may be in accordance with conventional valves.

In another embodiment, one or more openings/portions along the flowpath of the composition through and out of the device 1 are positioned such that when the device is not actuated (no delivery of composition) the openings/portions provide an incomplete flowpath and, thus, prevent delivery of the artificial tear composition. For example, in one embodiment as shown in FIGS. 9 and 10, the outlet port 6 may be in communication with the tubing 8, which is connected to the outlet via pathways as shown. Along the pathway, an opening, for example, as shown by 12, can be positioned such that it is not in communication with the pathway of the tubing 8 then the device is not actuated. This opening can, for example, be the only connection in the flowpath between the outlet 6 and the tubing 8. Upon actuation, (e.g. pressing the actuation mechanism 4 downwards), the portion having the opening 12 moves downwards within portion 14 to provide a complete flowpath between the outlet port 6 and tubing 8. Any known combination of openings and/or bores in a flowpath conventionally used in delivery devices can be used.

The device is used to deliver the artificial tear composition as a spray or mist. In a preferred embodiment, the device is designed to deliver artificial tears to the ocular surface and is designed accordingly. For example, the size of the diameter of the discharged spray or mist can be modified, for example, by providing outlet port(s) of particular sizes and configurations. Preferably, the device is designed so that, when the outlet port is positioned at a particular distance from the eye, the spray or mist is delivered to the eye and is not delivered to the surrounding facial areas. For example, the average cornea of the eye is approximately 11 mm in diameter and the average exposure ocular surface (i.e., exposed cornea and conjunctiva when the eyelids are open) is elliptical in shape measuring approximately 15 mm in height centrally and 30 mm in width. Thus, when the device is positioned at the proper distance from the eye and the spray or mist delivered, the diameter of the spray or mist when it reaches the surface of the eye is no greater than 30 mm. Because the ocular surface is elliptical in shape, the spray or mist is preferably delivered in an elliptical shape. As such, the greatest "height" of the spray or mist is no greater than 15 mm and the greatest "width" of the spray or mist is no greater than about 30 mm. When used, the device is preferably positioned with its length running vertically. As such, the elliptical shaped spray will be properly positioned with respect to the eye geometry. Of course, other positionings of the device can be used with the spray shape being properly delivered to the eye as required. In one embodiment, the substance can be delivered to the eye while preventing delivery to the facial areas surrounding the eye by further providing a funnel-like or similar extension 16 surrounding and extending from the outlet port as shown in FIG. 10. Thus, during use, the funnel-like or similar extension 16 could be placed in proximity to the eye or could even be placed against the face so as to surround the eye to prevent the substance from being delivered outside of the eye area. The funnel-like or similar extension 16 could also assist a user in positioning the device at the proper distance from the eye. Nonetheless, delivery of the artificial tear composition to the surrounding facial areas would not be particularly undesirable. The composition delivered by the present device is preferably a substantially "pure" composition free of additional, unnecessary ingredients (e.g. propellants and stabilizing agents), which some may find offensive if delivered to the skin.

In use, the delivery device 1 is held within a user's hand and the outlet port(s) 6 positioned in front of the eye. Because the device delivers the artificial tear composition in the form of a spray or mist, the user's head can remain facing forwards and the user need not recline his or her head as required with drop-like dispensing devices. The actuation mechanism 4 is manipulated, for example, by depressing a spray nozzle 5 downwards towards the housing, and the spray or mist is delivered to the eye. The process can be repeated if additional artificial tears need be administered.

The present invention also includes kits that comprise one or more devices of the invention, preferably packaged in sterile condition. Kits of the invention may also include written instructions for use of the devices and other components of the kit.

The foregoing description of the invention is merely illustrative thereof, and it is understood that variations and modifications can be effected without departing from the scope or spirit of the invention as set forth in the following claims. For example, although the present invention is described in detail in connection with delivery of an artificial tear composition to the ocular surface, the present invention is not limited to use on the eye and is not limited to delivery of artificial tears. Rather, the present invention may be used on other areas of the body to deliver various compositions to treat various conditions.

What is claimed is:

1. A device for the delivery of a substance to the eye comprising:
    a housing for holding the substance; and
    a non-aerosol, non-electric delivery mechanism comprising a tubular member disposed within the housing, an actuation mechanism positioned at the top of the housing, and at least one outlet port in the actuation mechanism in communication with the tubular member,
    wherein actuation of the actuation mechanism delivers the substance from the housing, through the tubular member, through the outlet port, and to the eye in the form of a spray or mist in a substantially horizontal direction, and
    wherein the outlet port is sized to deliver the spray or mist to the eye, the spray or mist having a circular or elliptical shape at a distance between 5 cm and 30 cm away from the outlet port, the elliptical shaped spray or mist having a height of no greater than 15 mm and a width of no greater than 30 mm.

2. The device of claim 1, wherein the substance is an artificial tears or demulcent composition and wherein the substance is delivered in an elliptical shape.

3. The device of claim 1, wherein the force of the spray or mist is sufficient to deliver the spray or mist to the eye without the aid of gravity.

4. The device of claim 1, wherein the housing is hollow and the substance is contained within the hollow of the housing.

5. The device of claim 1, wherein the housing contains a reservoir that holds the substance.

6. The device of claim 1, wherein the housing is fabricated of a rigid material to prevent collapse of the housing during use.

7. The device of claim 1, wherein the housing is hollow and walls forming the housing have a thickness sufficient to prevent collapse of the housing during use.

8. The device of claim 1, wherein the housing is fabricated of a translucent material.

9. The device of claim 1, wherein the housing is cylindrical in shape.

10. The device of claim 1, wherein the housing is at least 0.75 inch in length.

11. The device of claim 1, wherein the housing is at least 0.15 inch in its greatest cross-sectional width.

12. The device of claim 10, wherein the housing is between about 2.5 inches to about 5 inches in length.

13. The device of claim 11, wherein the housing is between about 0.2 inch and 2 inch in its greatest cross-sectional width.

14. The device of claim 1, wherein the housing is hollow and walls of the housing have a thickness of at least about 0.1 mm.

15. The device of claim 12, wherein the thickness of the walls is between about 0.1 mm to about 3 mm.

16. The device of claim 1, wherein the actuation mechanism is rotatable with respect to the housing such that rotating the actuation mechanism with respect to the housing delivers the substance to the eye.

17. The device of claim 1, wherein the actuation mechanism is movable upwards and/or downwards with respect to the housing such that movement of the actuation mechanism upwards and/or downwards with respect to the housing delivers the substance to the eye.

18. The device of claim 1, wherein the actuation mechanism includes a spray nozzle.

19. The device of claim 18, wherein the spray nozzle is positioned at the top of the housing and is movable downwards towards the housing such that moving the spray nozzle downwards causes the substance to be delivered to the eye.

20. The device of claim 18, wherein spray nozzle is rotatable with respect to the housing such that rotation of the spray nozzle delivers the substance to the eye.

21. The device of claim 1, further comprising a non-aerosol pump for delivery of the substance to the eye.

22. The device of claim 1, further comprising a non-electrically produced pump for delivery of the substance to the eye.

23. The device of claim 22, wherein the non-electrically produced pump is a non-piezoelectric or non-electromagnetic pump.

24. The device of claim 1, wherein the substance is delivered to the eye in the form of a spray or mist having a force less than that of an aerosol or electrically produced spray or mist.

25. The device of claim 1, wherein the force of the spray or mist delivered by the device is manipulated by varying the size of the outlet port.

26. The device of claim 1, wherein the force of the spray or mist delivered by the device is manipulated by varying the flow of substance through the outlet port.

27. The device of claim 1, wherein the delivery mechanism further comprises a valve, wherein the valve allows and prevents the delivery of substance to the eye.

28. The device of claim 27, wherein the valve is a pressure-responsive valve.

29. The device of claim 1, wherein the device has a flowpath for the substance from the housing and out of the outlet port, and wherein the device further includes one or more portions along the flowpath that block the flowpath when the delivery of the substance is prevented and wherein the one or more portions along the flowpath open the flowpath when the substance is delivered.

30. The device of claim 1 further comprising an extension substantially or completely surrounding the outlet port and extending in the direction that the spray or mist is delivered wherein the extension assists in directing the substance to the eye and assists in preventing the substance from being delivered to areas outside of the eye.

31. A method for the delivery of an artificial tears composition to the ocular surface comprising:
providing a device in accordance with claim 1; and
delivering the composition to the ocular surface, wherein delivery is not dependent on gravitational forces.

32. The method of claim 31, wherein the step of delivering the composition to the ocular surface comprises delivering the composition to the ocular surface in the form of a non-aerosol spray or mist.

33. The method of claim 32, wherein the step of delivering the composition to the ocular surface comprises delivering the composition to the ocular surface in the form of a non-electrically produced spray or mist.

34. The method of claim 33, wherein the composition is delivered to the ocular surface in the form of a non-piezoelectric or non-electromagnetic spray or mist.

35. A method for the delivery of an artificial tear composition to the ocular surface comprising:
providing a device in accordance with claim 1; and
delivering the composition to the ocular surface in the form of a spray or mist in a generally horizontal direction.

36. The method of claim 35, wherein the device further comprising an actuation mechanism in connection with the delivery mechanism and the method further comprises manipulating of the actuation mechanism to deliver the composition to the ocular surface.

37. The method of claim 36, wherein the actuation mechanism is rotatable with respect to the housing and wherein the step of manipulating the actuation mechanism comprises rotating the actuation mechanism with respect to the housing.

38. The method of claim 36, wherein the actuation mechanism is movable upwards and/or downwards with respect to the housing and wherein the step of manipulating the actuation mechanism comprises moving the actuation mechanism upwards and/or downwards with respect to the housing.

39. The method of claim 35, wherein the delivery mechanism includes a non-aerosol pump and the method further comprises activating the pump to assist in delivering the composition to the ocular surface.

40. The method of claim 35, wherein the step of delivering the composition to the ocular surface in the form of a spray or mist in a generally horizontal direction provides for delivery of the composition in the form of a spray or mist having a force less than that of an aerosol or electrically produced spray or mist.

41. The method of claim 35, wherein the method further comprises manipulating the force of the spray or mist delivered by the device by varying the size of the outlet port.

42. The method of claim 35, wherein the method further comprises manipulating the force of the spray or mist delivered by the device by varying the flow of substance through the outlet port.

43. The method of claim 35, wherein the method further comprises manipulating the force of the spray or mist delivered by the device by varying the proximity of the outlet port with respect to the ocular surface.

44. The method of claim 36, wherein the method further comprises manipulating the force of the spray or mist delivered by the device by utilizing varying amounts of force on the actuation mechanism.

45. The method of claim 35, wherein the device further comprises one or more valves and wherein the method further comprises opening the valve to allow for delivery of the composition.

46. A method for the delivery of a substance to the ocular surface of a patient comprising:
providing a device in accordance with claim 1; and
positioning the device in front of the eye a distance away from the eye without contacting the eye with any portion of the device, wherein the outlet port is in the line of sight with the housing in an upright position with the actuation mechanism and outlet port positioned at the top of the housing; and
delivering the substance to the eye as a spray or mist in a generally horizontal direction.

47. The device of claim 1, wherein the device is reusable.

48. The device of claim 1, wherein the device is disposable.

49. The device of claim 1, wherein the actuation mechanism is removable.

50. The device of claim 47, wherein the housing is refillable with the substance.

51. The device of claim 47, wherein the housing is configured to hold one or more refill cartridge holding the substance.

52. The device if claim 47, wherein the housing is replaceable with new housings holding the substance.

53. A device for treating the eye comprising:
a housing holding one or more substances and being free of propellant;
a non-aerosol, non-electric delivery mechanism comprising a tubular member disposed within the housing and at least one outlet port in communication with the tubular member, wherein actuation of the delivery mechanism delivers the substance to the eye in a substantially horizontal direction via the tubular member and outlet port in the form of a spray or mist, and
wherein the outlet port is sized to deliver the spray or mist to the eye, the spray or mist having a circular or elliptical shape at a distance between 5 cm and 30 cm away from the outlet port, the elliptical shaped spray or mist having a height of no greater than 15 mm and a width no greater than 30 mm.

54. The device of claim 1, wherein the outlet port delivers the spray or mist in an elliptical shape.

* * * * *